United States Patent
Welt et al.

(10) Patent No.: US 8,246,617 B2
(45) Date of Patent: Aug. 21, 2012

(54) SURGICAL SNARE WITH ELECTROSURGICAL TIP AND METHOD OF USE

(75) Inventors: Robert E. Welt, Wake Forest, NC (US); William L. Athas, Chapel Hill, NC (US); Thomas B. Miller, Perkiomenville, PA (US)

(73) Assignee: TransEnterix, Inc., Durham, NC (US)

( * ) Notice: Subject to any disclaimer, the term of this patent is extended or adjusted under 35 U.S.C. 154(b) by 165 days.

(21) Appl. No.: 12/469,071

(22) Filed: May 20, 2009

(65) Prior Publication Data

US 2011/0082456 A1    Apr. 7, 2011

Related U.S. Application Data

(63) Continuation-in-part of application No. 12/209,586, filed on Sep. 12, 2008.

(60) Provisional application No. 60/971,900, filed on Sep. 12, 2007.

(51) Int. Cl.
A61B 18/18    (2006.01)

(52) U.S. Cl. ............... 606/45; 606/41; 606/52

(58) Field of Classification Search ............... 606/37, 606/46, 52, 190, 206, 207, 51, 41, 45
See application file for complete search history.

(56) References Cited

U.S. PATENT DOCUMENTS

| | | | | |
|---|---|---|---|---|
| 5,226,429 | A | * | 7/1993 | Kuzmak ............... 128/898 |
| 5,304,183 | A | | 4/1994 | Gourlay et al. |
| 5,697,931 | A | | 12/1997 | Thompson |
| 6,066,090 | A | | 5/2000 | Yoon |
| 2001/0049497 | A1 | | 12/2001 | Kalloo et al. |
| 2003/0212429 | A1 | | 11/2003 | Keegan et al. |
| 2007/0038230 | A1 | | 2/2007 | Stone |
| 2007/0288035 | A1 | | 12/2007 | Okada |
| 2008/0009854 | A1 | * | 1/2008 | Yates .................. 606/42 |
| 2009/0157076 | A1 | | 6/2009 | Athas et al. |

FOREIGN PATENT DOCUMENTS

| | | |
|---|---|---|
| EP | 1 586 275 A | 10/2005 |
| WO | WO 2006-110275 | 10/2006 |
| WO | WO 2009-035650 A2 | 3/2009 |

OTHER PUBLICATIONS

International Search Report for PCT/US2008/010640, mailed May 19, 2009, 1 page.*

* cited by examiner

*Primary Examiner* — Bhisma Mehta

(57) ABSTRACT

A medical device includes a tissue dissector and a snare loop on a common shaft. At least the distal tip of the snare loop is energizable to function as an electrosurgical element for tissue dissection. In use the snare loop is partially extended from the shaft to expose the electrosurgical element for electrosurgical dissection, and the snare loop is fully extended from the shaft to deploy the snare loop for retrieval and positioning of an implant such as a gastric banding device. The snare loop may be deployed through a pair of jaws also mounted on the shaft for use in tissue dissection.

5 Claims, 10 Drawing Sheets

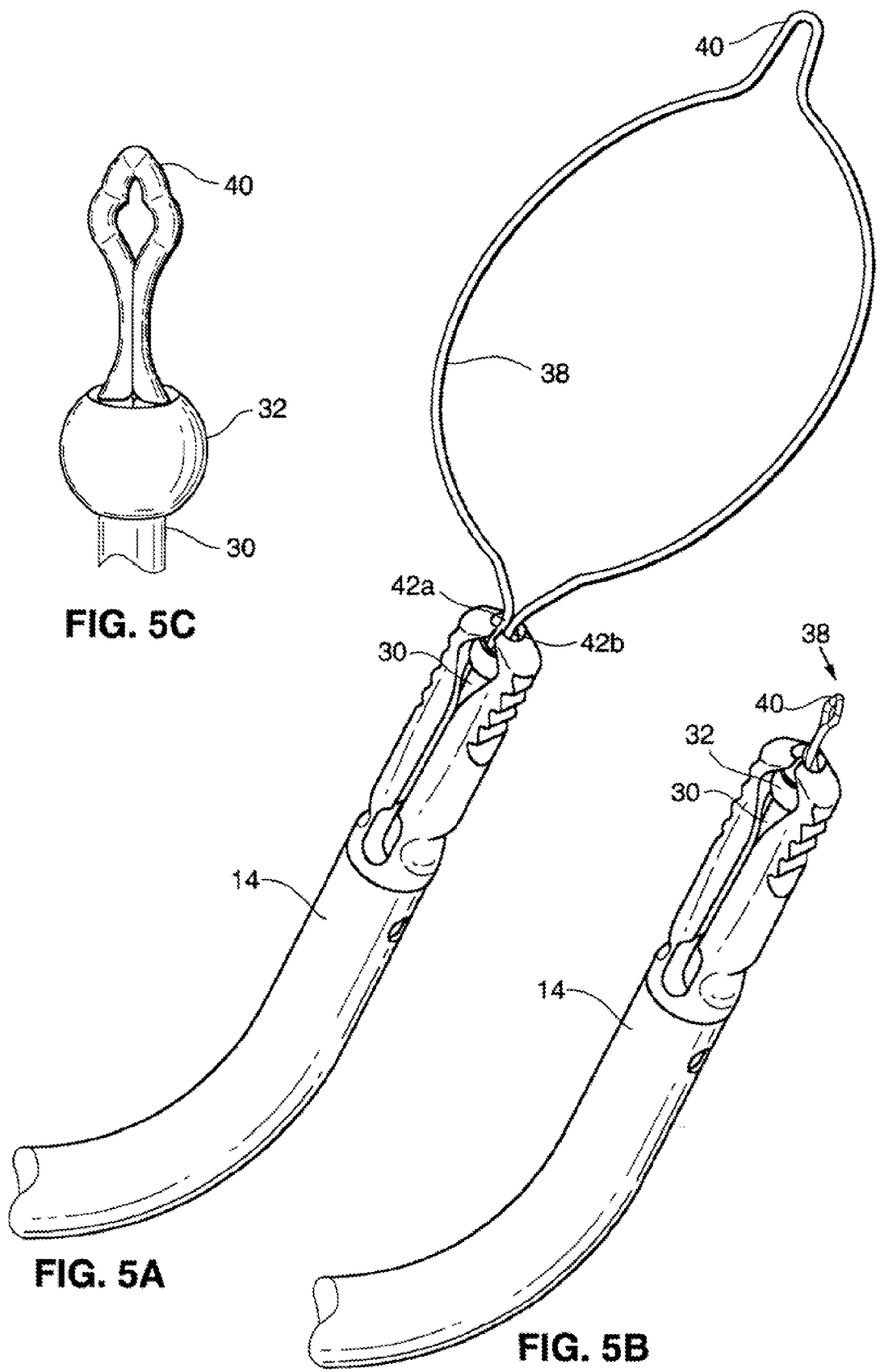

SURGICAL SNARE WITH ELECTROSURGICAL TIP AND METHOD OF USE

RELATED APPLICATIONS

This application is a continuation in part of U.S. application Ser. No. 12/209,586, filed Sep. 12, 2008, which claims the benefit of U.S. Provisional Application No. 60/971,900, filed Sep. 12, 2007.

TECHNICAL FIELD OF THE INVENTION

The present invention relates to the field of systems for performing surgical procedures through minimally invasive access ports.

BACKGROUND

Co-pending U.S. application Ser. No. 12/209,586, filed Sep. 12, 2008 and incorporated herein by reference, describes procedures and devices useful for implanting a gastric banding device (e.g. lap band or Swedish lap band) using a minimally invasive technique.

In accordance with one of the disclosed implantation procedures, one or more dissection instruments is passed through single port or laparoscopic access devices and used to dissect a tunnel around the posterior side of the stomach, through the fascia/connective tissue surrounding the proximal stomach and lower esophagus. A snare is advanced through the tunnel and positioned with the shaft of the snare device extending through the tunnel and with the loop of the snare accessible from or near the anterior side of the stomach. A portion of the gastric band is passed through the open snare loop and the snare loop is closed to engage the gastric band. Tension is applied to the snare to withdraw the snare back around the posterior side of the stomach and then anteriorly in order to draw the gastric band around the posterior side of the stomach. The gastric band is closed around the stomach.

The prior application describes a combination dissection and snare device particularly beneficial for carrying out the procedure. That device is disclosed as having an elongate shaft having a pre-curved distal end and an optional dissection balloon positioned on the shaft. A monopolar RF dissection wire is positioned within the shaft and has a conductive tip or electrode extendable from the shaft when needed to electrosurgically dissect or penetrate tissue. A snare loop is also extendable from and retractable into the distal end of the shaft. That device simplifies implantation of a gastric banding device in that it allows the dissection step(s) and the step of engaging the implant to be carried out with a single device. In particular, the device is advanced into the abdominal cavity, and manipulated using RF and/or blunt dissection to form an appropriate path through the connective tissue. As the device is advanced to the posterior side of the stomach, the curvature of the device carries the distal end of the device into a more anterior position. The snare is deployed from the device. The gastric band is passed into the cavity, captured using the snare, and drawn around the posterior side of the stomach using the snare.

The present application describes an improvement to the combination dissection device and snare disclosed in the prior application.

BRIEF DESCRIPTION OF THE DRAWINGS

FIG. 5A is similar to FIG. 4 but shows the snare fully extended.

FIG. 5B is similar to FIG. 5A but shows the snare partially extended.

FIG. 5C is a close-up view of the partially extended snare.

The present application describes a medical instrument having an elongate shaft and a snare extendable from the distal portion of the shaft. In an exemplary method of using the medical instrument, the instrument is used to position a band around a stomach in a body cavity. According to the exemplary method, the elongate shaft is introduced into the body cavity. A distal tip of the snare loop is advanced from the shaft to a first position in which the distal tip is distal to the shaft. The distal tip is energized using a source of electrosurgical energy. The shaft is advanced in a first direction to form a tunnel through tissue around a portion of the stomach using the energized distal tip. In some embodiments, the shaft includes jaws, and the distal tip may be advanced from a distal end of the jaws. The jaws may be dissecting jaws, and the tunnel may be expanded using the dissecting jaws. In some embodiments, expanding the tunnel using the dissecting jaws is performed during advancement of the shaft to form the tunnel using the energized tip. In some embodiments, expanding the tunnel includes, after forming the tunnel, withdrawing the shaft in the second direction while manipulating the jaws to expand the tunnel.

With the shaft disposed in the tunnel, the snare loop is advanced to a second position in which the snare loop is distal to the shaft. A portion of a gastric banding device is passed through the snare loop. The snare loop is partially withdrawn relative to the shaft to close the snare loop against the banding device. The shaft is withdrawn in a second direction opposite to the first direction to draw a portion of the gastric banding device through the tunnel. The gastric banding device is retained around the stomach.

DETAILED DESCRIPTION

Figure 1:
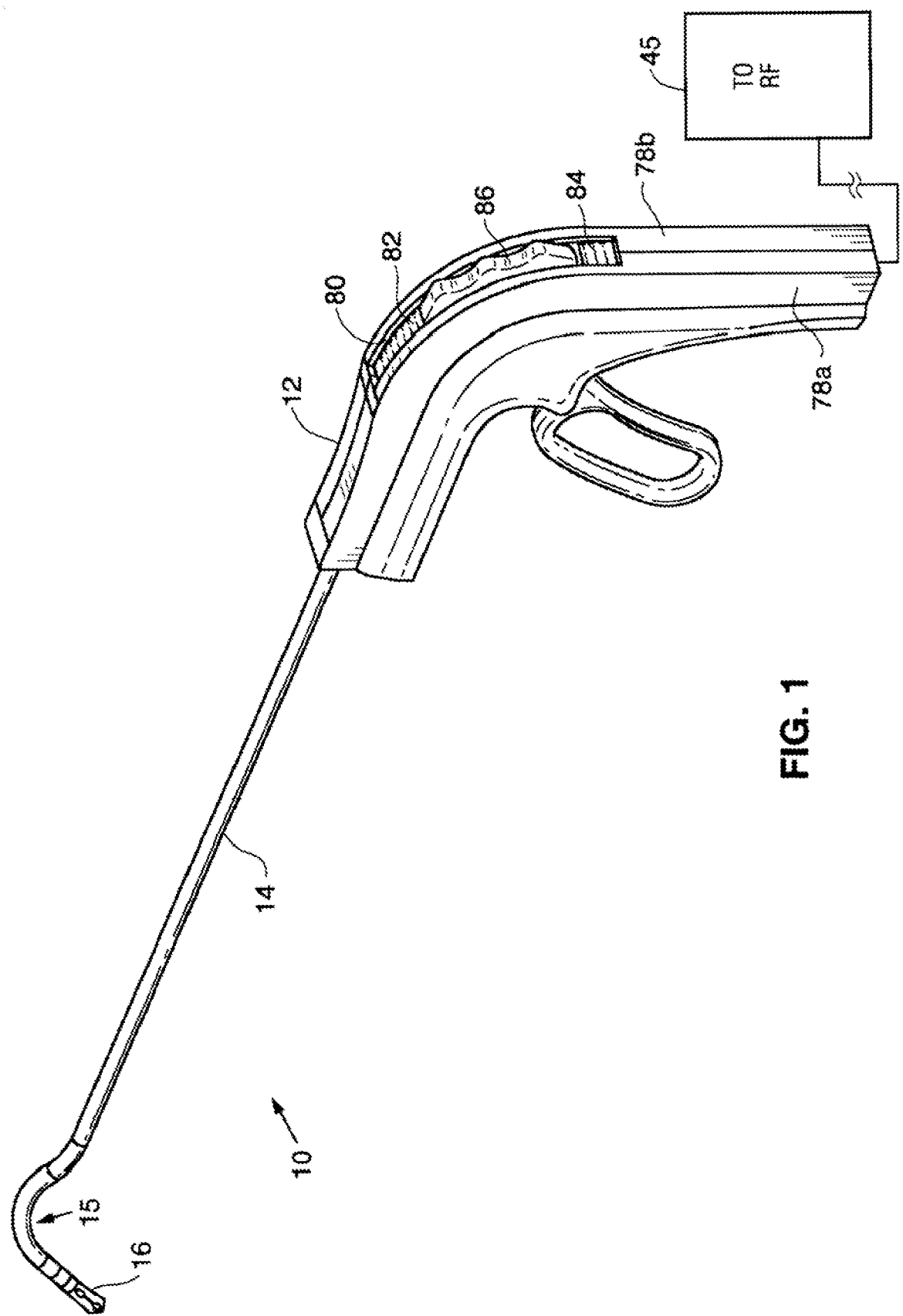
FIG. 1 is a perspective view of the electrosurgical dissector and snare device.

FIG. 1 shows an embodiment of a combination electrosurgical dissector and snare device 10. Dissector and snare device 10 has a handle 12 and an elongate shaft 14 having a pre-curved distal section 15. The shaft is preferably rigid or semi-rigid so as to allow it to approximately retain its shape during use, although in alternative embodiment flexible shafts may be used.

Figure 2A:
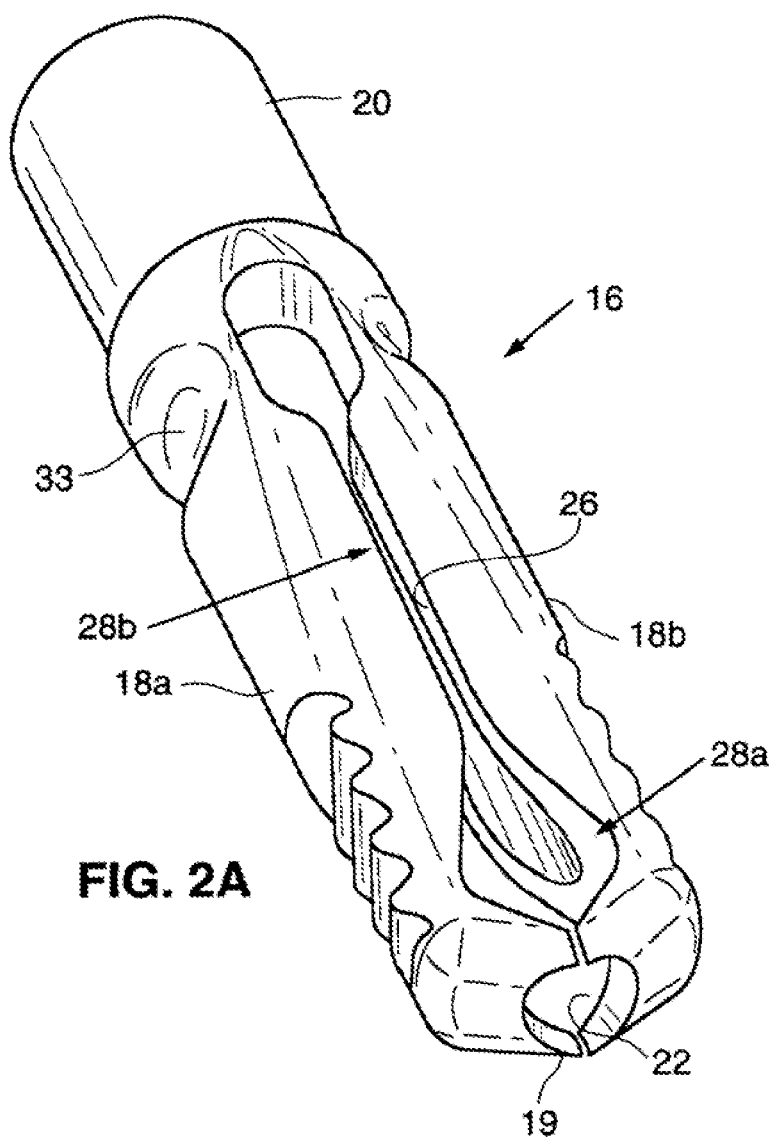
FIG. 2A is a perspective view of the jaw tip of the device of FIG. 1

A jaw tip 16 is positioned at the distal end of the shaft 14. Referring to FIG. 2A, in one embodiment, the jaw tip 16 is a tubular element having integrally formed first and second jaw members 18a, 18b extending from a tubular coupling 20. The single piece construction of the jaw tip biases the jaw members 18a, 18b in the closed position shown in FIG. 2A. Each jaw member has a pair of teeth 19 extending towards the opposed jaw member. When in the closed position, the jaw members 18a, 18b define a distal gap or passage 22 at their distal ends.

Figure 2B:
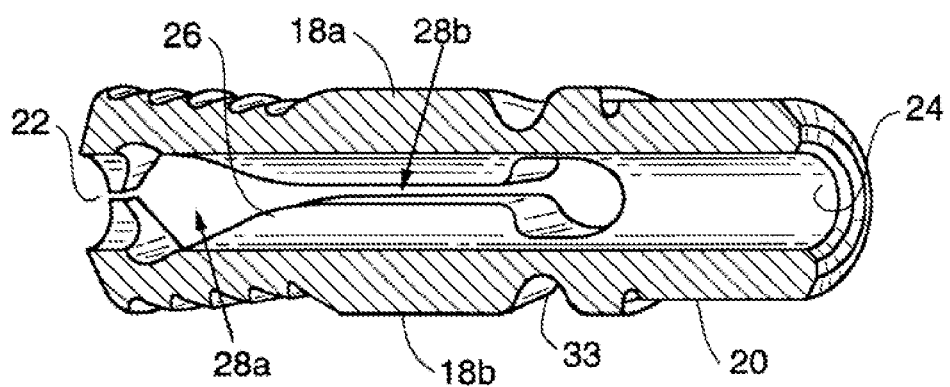
FIG. 2B is a longitudinal cross-section view of the jaw tip of FIG. 2.

Referring to FIG. 2B, the jaw tip 16 includes a cylindrical lumen 24 aligned with the passage 22. Walls defining the lumen 24 having longitudinally-extending edges 26 between the jaw members 18a, 18b. The edges 26 define a space between the jaw members 18a, 18b. Due to the varying contour of the edges 26, the space has a broad distal section 28a and a narrow section 28b proximal to the distal section 28a.

Figure 4A:
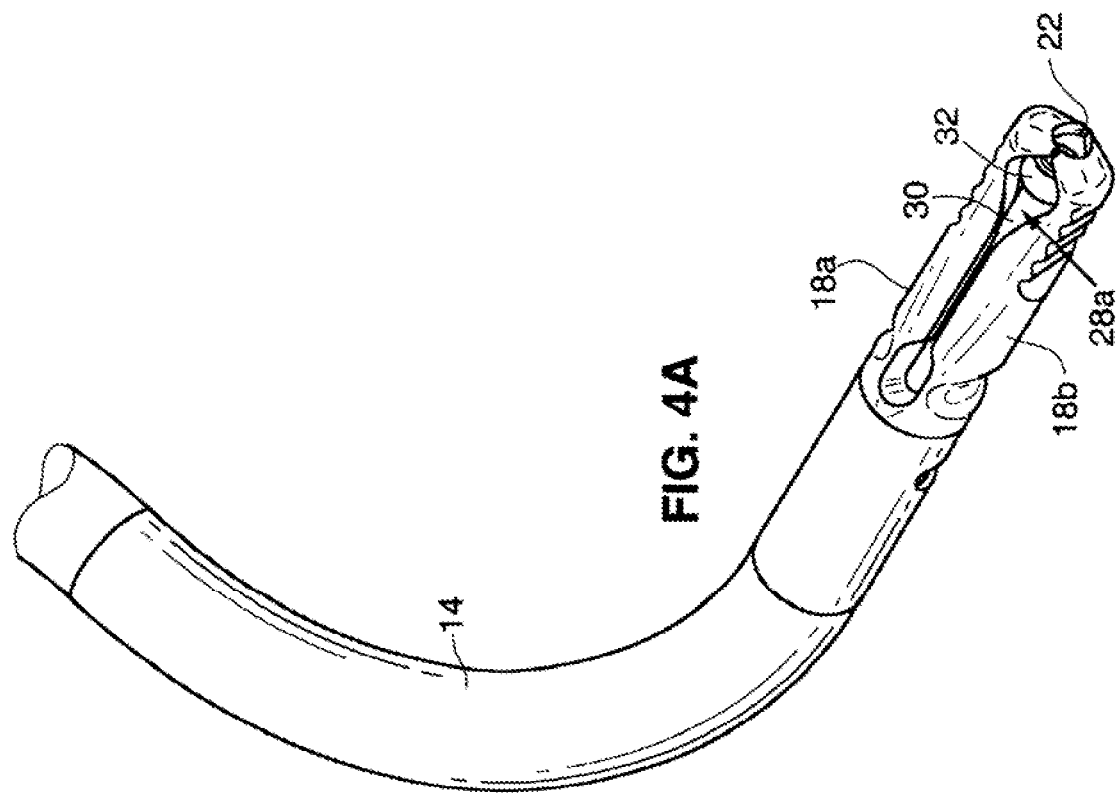
FIG. 4A is similar to FIG. 3 but includes the jaw tip.
Figure 3:
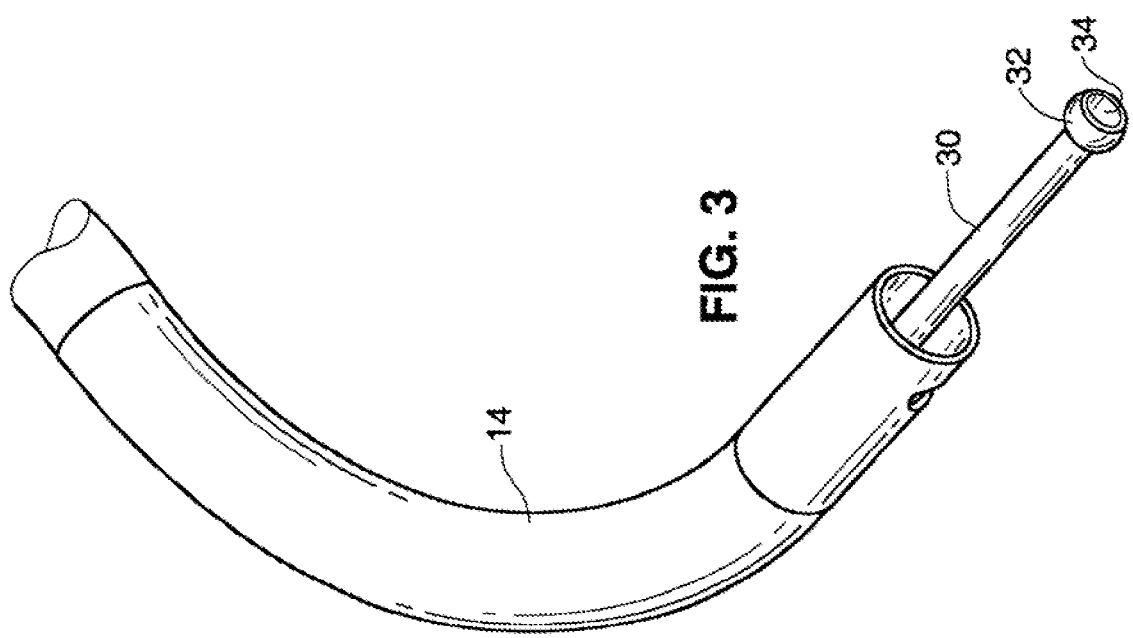
FIG. 3 is a perspective view of the distal end of the device, with the jaw tip removed.

The distal end of the shaft 14, with the jaw tip 16 removed, is shown in FIG. 3. A snare guide tube 30 extends through the lumen of the shaft 14. A distal element 32 is positioned at the tip of the guide tube 30 and has an opening 34 aligned with the lumen of the snare guide tube 30. In the illustrated embodiment, the distal element 32 is a spherical bead, the surface of which, as shown in FIG. 4A, extends into the broad distal section 28a of the space between the jaw members 18a, 18b. The opening 34 in the distal element 32 is aligned with the distal passage 22 defined by the jaws in the closed position.

Figure 4B:
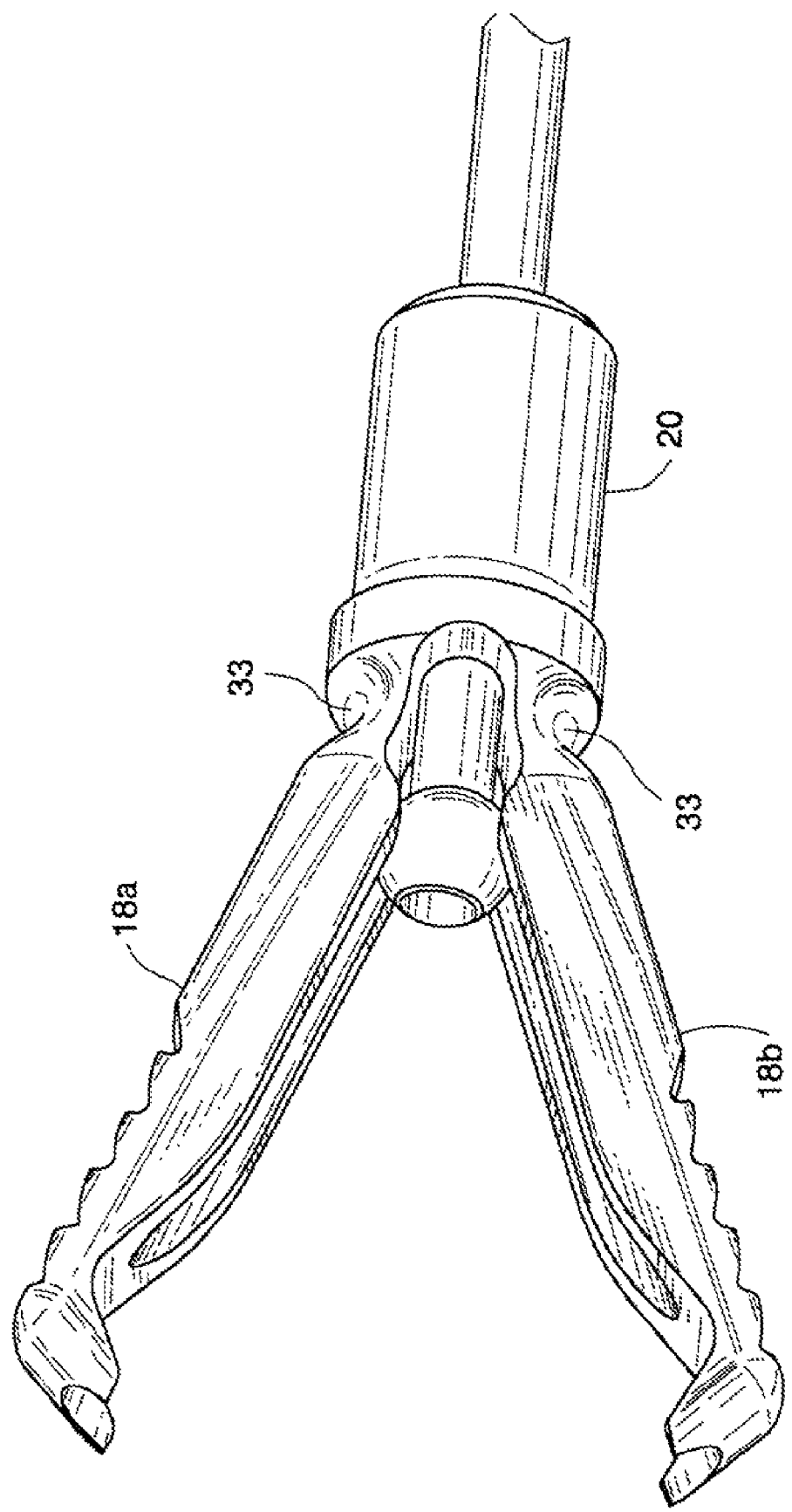
FIG. 4B is a perspective view of the distal end of the device showing the jaws flexed into the opened position.
Figure 7A:
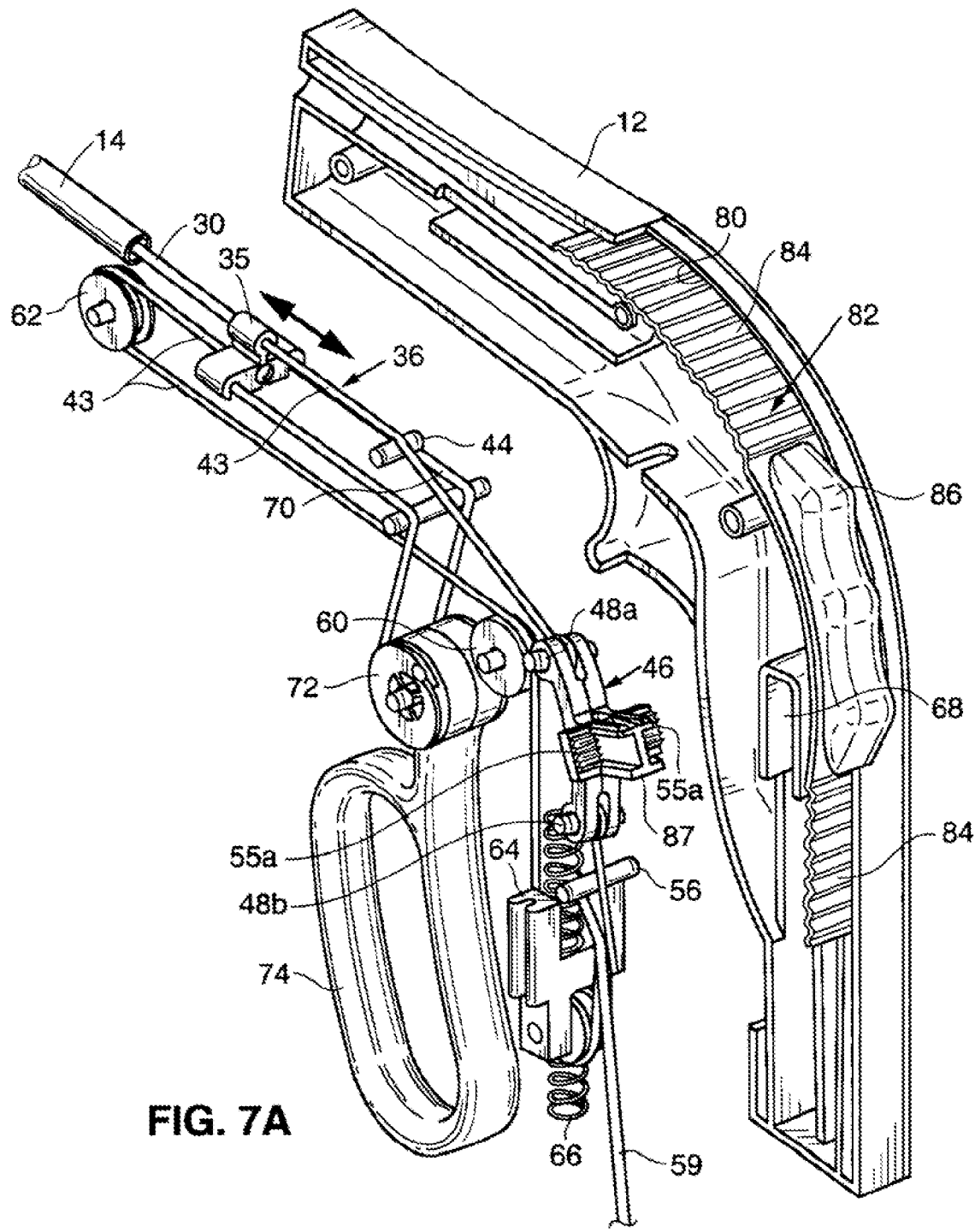
FIG. 7A is a partially exploded view of the handle in which one shell section of the handle housing is not shown.

Referring to FIG. 7A the proximal end of the snare guide tube 30 is coupled to a piston 35 disposed within the handle 12. As will be discussed in detail below, the piston 35 is longitudinally moveable within the handle to a retracted position to withdraw the snare guide tube 30 and thus its distal element 32 in a proximal direction. When the distal element is moved proximally, it cams the jaws to the open position shown in FIG. 4B as it moves from within the broad distal section 28a to the narrow section 28b of the space defined by the edges 26. As shown, the jaw members 18a, 18b flex at flex regions 33 when they are moved to the open position. When the distal element is returned to a more distal position within the broad section 28a, it moves out of contact with the edges 26, allowing the spring bias of the jaw members 18a, 18b to return them to the closed position.

A snare 36 is disposed within the snare guide tube 30. The snare 36 is formed of a wire strand formed into a loop 38. FIG. 5A shows the snare 36 in a fully deployed position in which the loop 38 is fully extended from the guide tube 30. A v-shaped tip section 40 is positioned at the distal end of the loop 38. The snare is advanceable from the fully retracted position shown in FIG. 4A in which the snare loop is fully contained within the snare guide tube 30, to a partially extended position shown in FIG. 5B in which the tip section 40 extends from the snare guide tube 30. When the snare loop is in the partially extended position, the portions of the wire loop just proximal to the "v" may extend in parallel contact with one another as shown in FIG. 5C. The snare loop is further advanceable to the fully deployed position shown in FIG. 5A. The snare 36 is formed of an electrically conductive wire so that the tip can function as an RF dissection wire. The snare 36 may be conductive only at the tip 40, with the remainder of the loop 38 covered by insulative material, or the entire loop 40 (including the tip 40) may be conductive.

Figure 6:
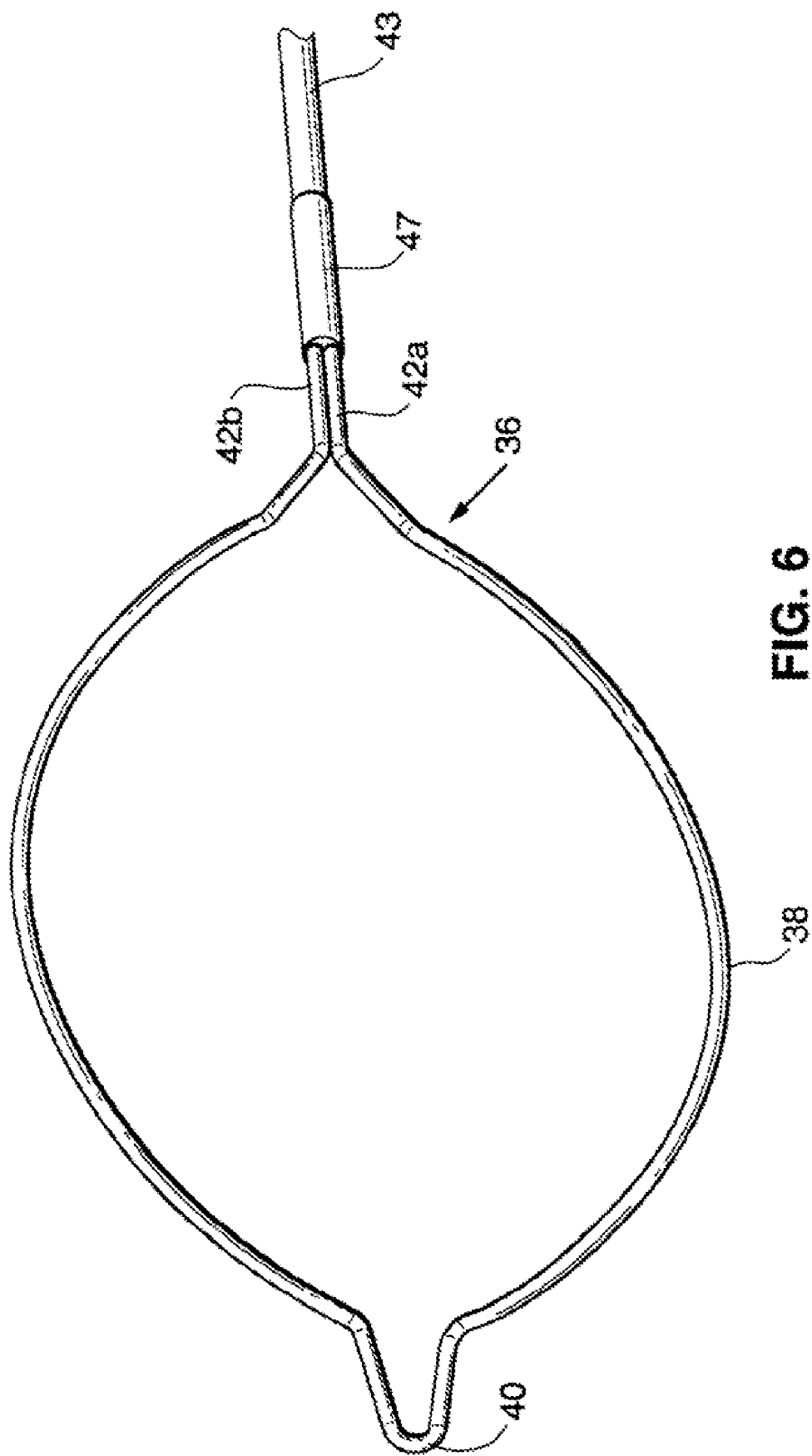
FIG. 6 is a perspective view of the snare removed from the snare guide tube and shaft.
Figure 7B:
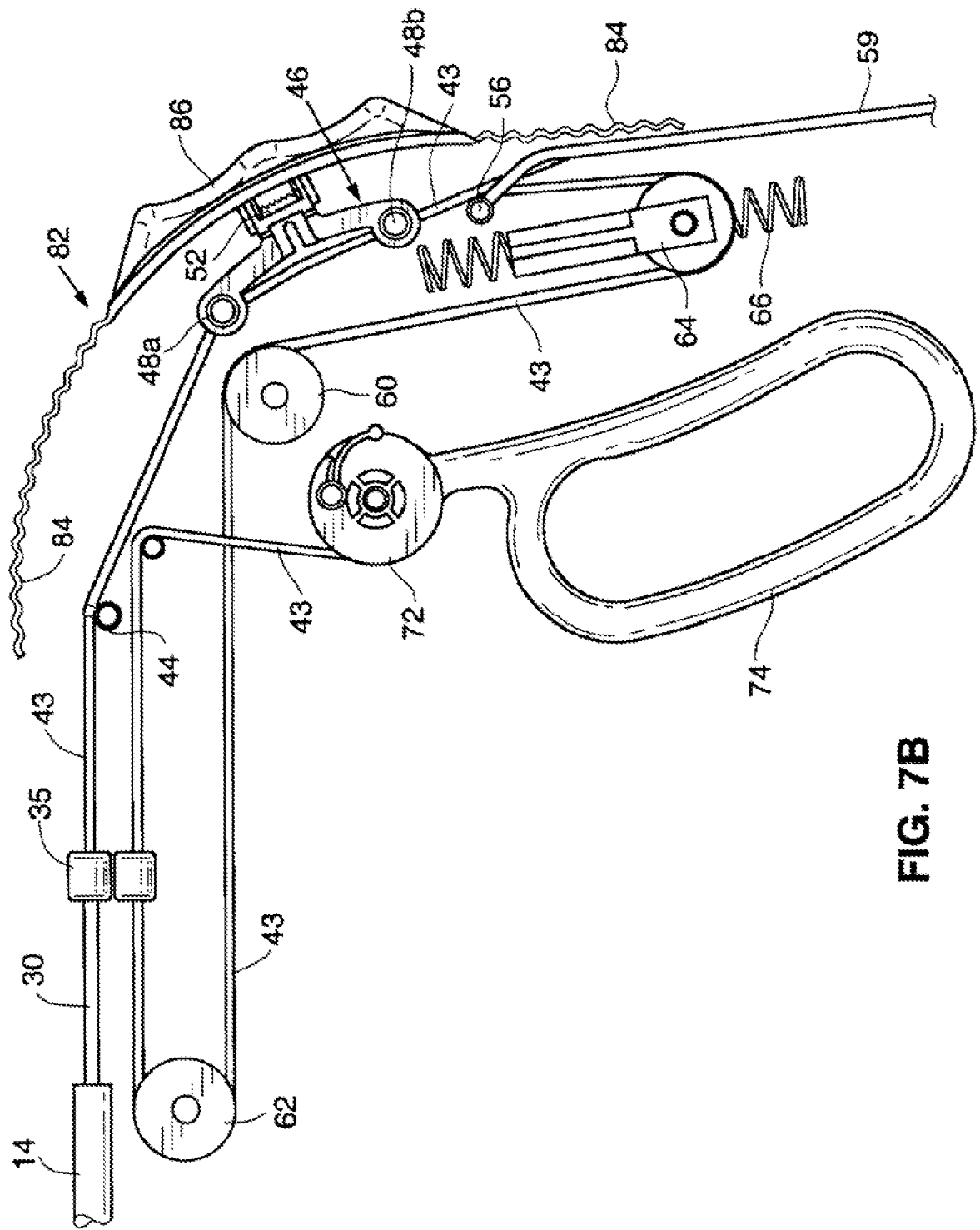
FIG. 7B is a side elevation of the contents of the handle without the housing.
Figure 8:
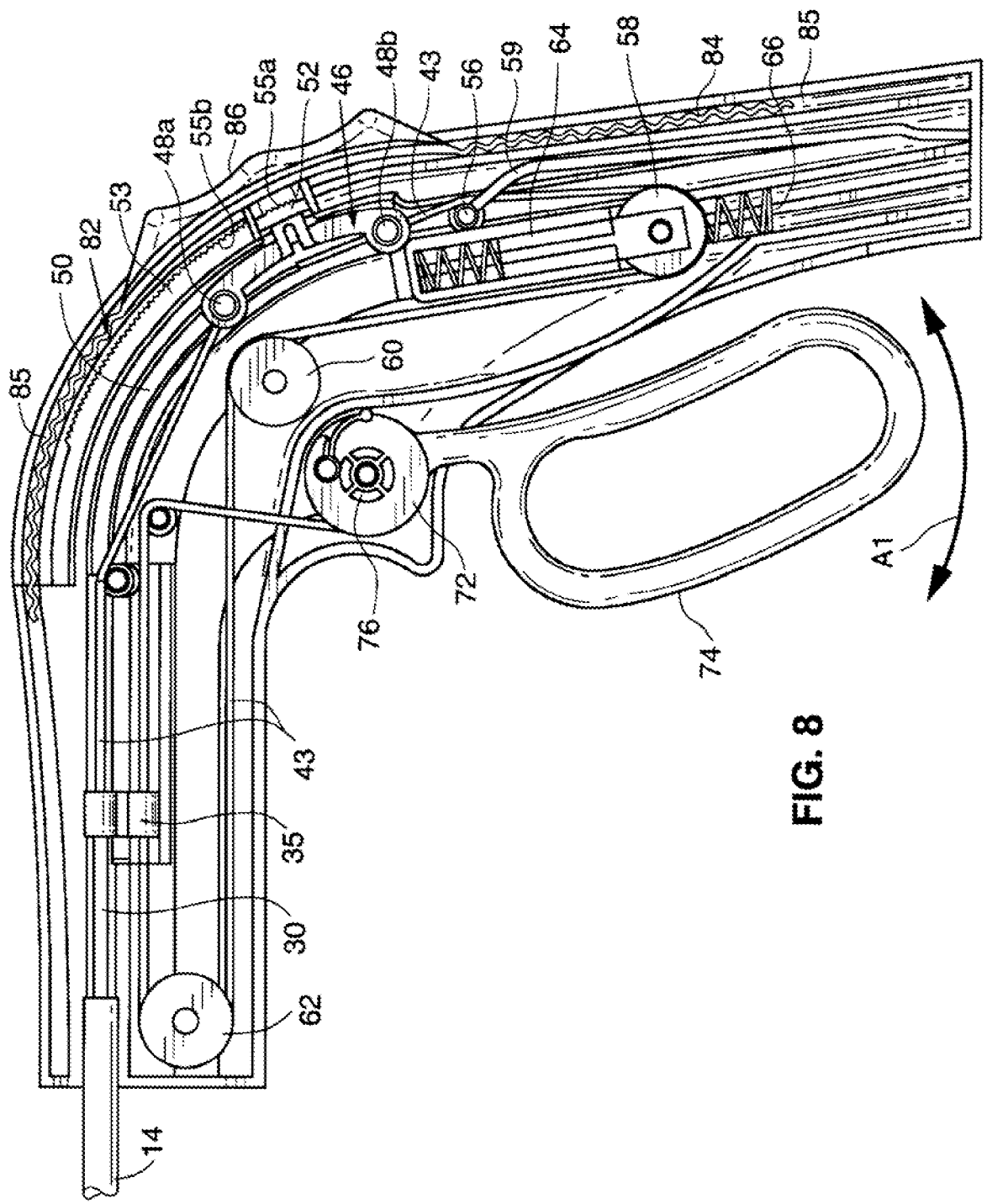
FIG. 8 is similar to FIG. 7B but shows one shell section of the housing.

As most easily viewed in FIG. 6, the snare 36 includes two parallel proximal end sections 42a, 42b of the snare wire. The end sections 42a, 42b are connected to a snare conductor 43 by soldering, using a short piece of tubing 47 to cover and complete the joint. Referring now to FIGS. 7A and 7B, the snare conductor 43 extends through the snare guide tube 30, around a pin 44, and is coupled to a slider 46. The slider 46 includes first and second pins 48a, 48b, each of which is connected to the snare conductor 43. As shown in FIG. 8, the ends of each pin 48a, 48b are slidably disposed in slots 50 in opposite sides of the handle housing (one side of which is shown). A head 52 on the slider 46 is slidably positioned within slots 53 parallel to the slots 50.

An upper surface of the head includes a sawtooth pattern of ridges 55a. Corresponding ridges 55b are formed in the slots 53 such that the ridges 55a, 55b engage one another to maintain the longitudinal position of the slider 46 within the slots 53.

The snare conductor 43 extends from the second pin 48b of the slider 46, around another pin 56 and a series of pulleys 58, 60, 62 and is coupled to a proximal side of the piston 35. Pulley 58 is supported by a bracket 64 mounted to a compression spring 66. The compression spring 66 is seated within a slot 68 (FIG. 7A) in the handle 12.

The snare conductor 43 is electrically coupled to an energy source such as a monopolar RF source 45 (FIG. 1). FIG. 7B shows that in the illustrated embodiment, a conductor 59 is coupled to one of the pins 56 with which the snare conductor 43 is in contact, so that the pin 56 electrically couples the snare conductor 43 to conductor 59.

A pair of jaw actuation cables 70 is connected to the piston 35. The cables 70 extend around a pin and are connected to spool 72 connected to a grip 74. The spool 72 is pivotally mounted within the handle 12 by a pin 76.

Referring again to FIG. 1, a preferred handle housing is comprised of shell halves 78a, 78b which, when assembled, leaved an exposed cutout 80. The cutout 80 is covered by a cover 82 having flexible end sections 84 that extend into the cutout 80. The cover 82 includes a button 86 disposed between the end sections 84. The button 86 is coupled to a standoff 87 (FIG. 7A) that extends towards the button 86 from the head 52 of slider 46 (FIG. 8). The sawtooth ridges 55b in the handle 12 (described with reference to FIG. 8) contact the head 52 on opposite sides of the standoff 87. Pressing the button 86 towards the cutout 80 depresses the head 52 to move the ridges 55a of the head out of engagement with the ridges 55b in the handle. Sliding the button 86 distally after disengaging the ridges 55a, 55b slides the slider 46 distally within the handle. When the button slides 86, its flexible end sections 84 slide within slots 85 (FIG. 8) in the housing.

Operation of the device 10 will next be described. A user will typically hold the device with his/her palm against the handle 12, his/her index finger extending through the grip 74, and his/her thumb on the button 86. To open the jaws 18a, 18b, the user squeezes the grip 74 towards the handle 12, causing the grip 74 and spool 72 to pivot relative to the pin 76 and to thus apply tension to the jaw actuation cables 70. The actuation cables 70 pull the piston 35 in a proximal direction and in doing so they withdraw the snare guide tube 30 proximally. The distal element 32 on the snare guide tube 30 spreads the jaws apart by camming the jaws into the open position by acting on the edges 26 as described above. Releasing the grip 74 causes the jaws to return to the open position under their own spring bias.

The features for retracting the snare guide tube 30 to open the jaws and for deploying the snare operate cooperatively to maintain the longitudinal alignment of the snare loop 38 and the snare guide tube 30. In particular, when the piston 35 is moved proximally to retract the snare guide tube 30, it pulls the distal end of the snare cable 43 (i.e. the portion anchored to the piston 35 near pulley 62) proximally, applying tension to the slider 46 and thus the portion of the snare cable 43 that extends into the snare guide tube 30, to retract the snare 36 by a corresponding amount. This avoids inadvertent exposure of the snare loop 38 when the jaws are opened. The bracket 64 and spring 66 act as a tensioning system to aid in maintaining the position of the snare loop 38 relative to the jaws 18a, 18b.

To extend the snare loop 38, the user presses button 86 using his or her thumb. The button 86 presses downwardly against the head 52 of the slider 46, releasing the engagement between the sawtooth ridges 55a, 55b. Once released, the slider 46 is free to slide longitudinally within the handle. The user advances the button 86 to slide the slider 46 in a distal direction, thus pushing the snare loop 38 from the distal end of the snare guide tube 30. Because of the passage 22 in the jaw tip, the snare loop 38 can be advanced whether the jaws are closed or open. It should be noted that the jaw tip 16 is preferably formed of material that is not electrically conductive so as to prevent conduction of RF energy from the snare to the jaws.

The user may advance the snare loop 38 by a first amount to expose only the tip 40 (FIG. 5B), or s/he may advance the snare loop 38 by a greater amount to fully deploy the snare (FIG. 5A). The user can engage the snare loop 38 in an extended position by releasing pressure against the button 86, allowing the sawtooth ridges of the head 52 to re-engage with the corresponding ridges in the handle.

When it is time to retract the snare loop 38, the user applies downward pressure to the button 86 to disengage the ridges 55a, 55b and s/he then retracts the button 86 proximally to return the slider to its original position.

Figure 9A:
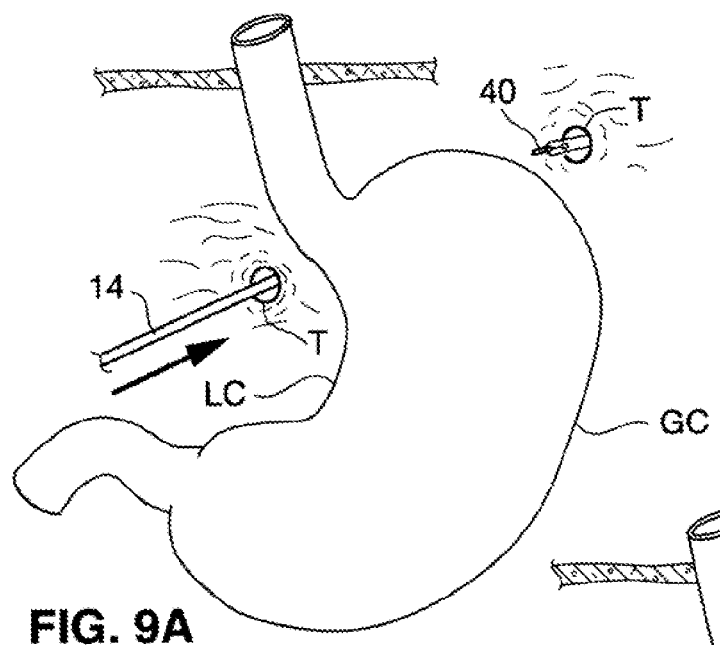
FIGS. 9A-9C are a sequence of drawings schematically illustrating use of the device for implantation of a gastric banding device.

In a typical procedure, the device 10 is advanced through a single port or laparoscopic access device into the abdominal cavity and advanced towards the stomach. The snare loop 38 is advanced to the position shown in FIG. 5B, exposing the tip 40. The snare loop 38 is energized by activating the RF energy source 45 (e.g. by depressing a foot pedal). The tip 40 is advanced around the posterior side of the stomach, electrosurgically forming a tunnel T through the fascia, connective tissue and/or other tissue posterior to the stomach as shown in FIG. 9A. The user may begin the electrosurgical step adjacent to the lesser curvature LC of the stomach and continue formation of the tunnel under the stomach to the greater curvature GC, or the electrosurgical step may be at the greater curvature and work towards the lesser curvature.

Figure 9B:
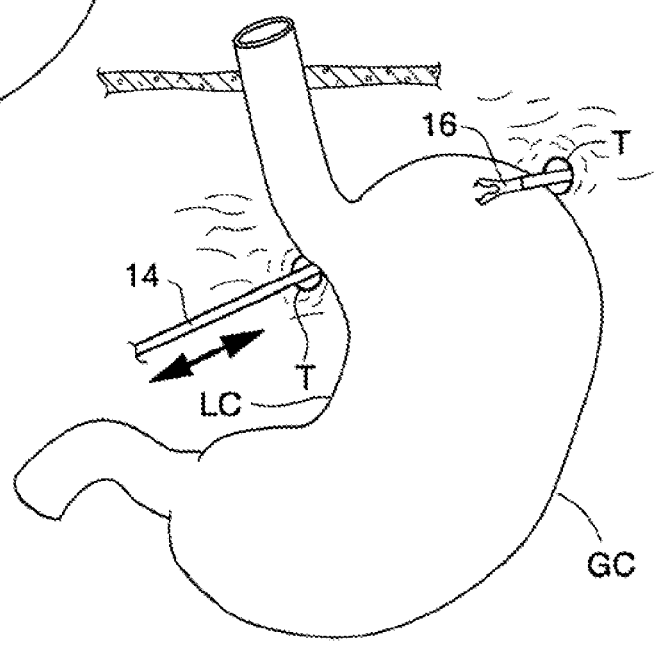
Figure 9C:
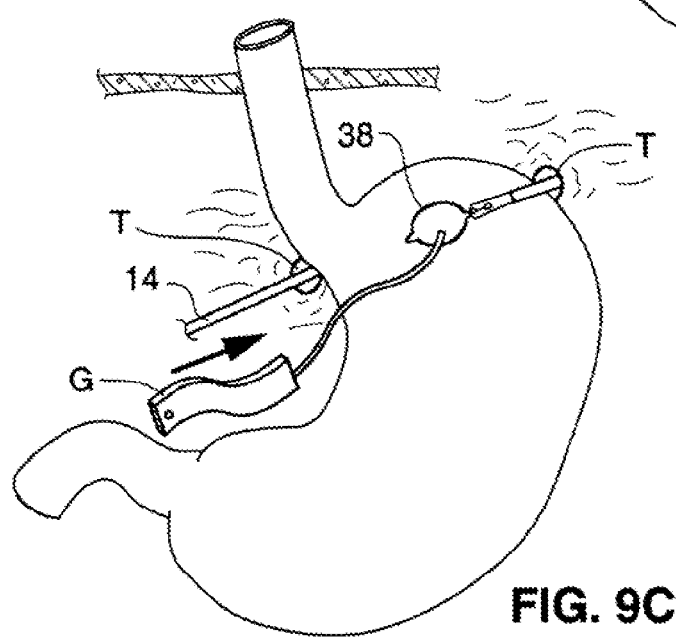

The electrosurgically formed tunnel T is expanded using the dissecting jaws 18a, 18b as shown in FIG. 9B. This step may be performed during the electrosurgical step, with the jaws being opened and closed behind the energized tip 40 as the tip 40 forms the tunnel through the tissue. Alternatively, or in addition to using the jaws during electrosurgical dissection, the distal end of the device may be retracted back through tunnel and the jaws used at that time (during retraction and/or subsequent re-advancement of the device within the tunnel) to increase the size of the tunnel using known dissection techniques. Use of the jaws for dissection can involve opening the jaws to separate tissue layers on opposite sides of the jaws The curvature of the distal section 15 aids in directing the operative tip around the stomach and into a more anterior position (FIG. 9C) appropriate for full deployment of the snare for retrieving the gastric band G. Once the tunnel has been dissected to an appropriate size, the snare is moved to the fully deployed position of FIG. 5A, and a portion of a gastric banding device is placed within the loop of the snare. The snare is withdrawn somewhat to cinch the loop against the gastric banding device. The device 10 is withdrawn, passing again around the posterior side of the stomach, thus drawing the engaged end of the gastric banding device with it. The banding device is closed into a loop and retained in place using known techniques. The dissector and snare device 10 is removed from the body cavity, leaving the banding device implanted around the stomach.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the claims and their equivalents.

Any and all applications referred to herein, including for purposes of priority, are hereby incorporated herein by reference.

We claim:

1. A method for positioning a band around a stomach in a body cavity, the method comprising:
   introducing an elongate shaft into the body cavity,
   positioning a snare within the elongate shaft, the snare including a snare loop and a distal tip on the snare loop;
   advancing the distal tip of the snare loop from the shaft to a first position in which the distal tip is distal to the shaft;
   energizing the distal tip using a source of electrosurgical energy and advancing the shaft in a first direction to form a tunnel through tissue around a portion of the stomach using the energized distal tip;
   with the shaft disposed in the tunnel, advancing the snare loop to a second position in which the snare loop is distal to the shaft;
   passing a portion of a gastric banding device through the snare loop and partially withdrawing the snare loop relative to the shaft to close the snare loop against the banding device;
   withdrawing the shaft in a second direction opposite to the first direction to draw a portion of the gastric banding device through the tunnel;
   and retaining the gastric banding device around the stomach.

2. The method of claim 1 wherein the method further includes expanding the
   tunnel using dissecting jaws disposed on the shaft.

3. The method of claim 2 wherein advancing the distal tip of the snare loop
   includes advancing the distal tip from a distal end of the jaws.

4. The method of claim 3 wherein expanding the tunnel using the dissecting
   jaws is performed during advancement of the shaft to form the tunnel using the energized tip.

5. The method of claim 2 wherein expanding the tunnel includes, after forming the tunnel, withdrawing the shaft in the second direction while manipulating the jaws to expand the tunnel.

* * * * *